United States Patent [19]

Cavaliere Vesely et al.

[11] Patent Number: 5,895,648
[45] Date of Patent: Apr. 20, 1999

[54] COMPOSITION FOR FEED USE COMPRISING LYOPHILIZED LIVE LACTIC BACTERIA

[75] Inventors: Renata Cavaliere Vesely, Milan; Giovanni Giani, Pasturago di Vernate; Gianluigi Maiocchi, Codogno; Marco Emilio Vesely; Leonardo Vesely, both of Milan, all of Italy

[73] Assignee: Sitia-Yomo S.p.A., Milan, Italy

[21] Appl. No.: 08/922,459

[22] Filed: Sep. 3, 1997

[30] Foreign Application Priority Data

Dec. 23, 1996 [EP] European Pat. Off. .............. 96830643

[51] Int. Cl.$^6$ .............................. A01N 63/00; C12N 1/20
[52] U.S. Cl. .................. 424/93.4; 424/93.3; 424/93.44; 424/93.45; 426/43; 426/62; 426/71; 426/658; 435/252.4; 435/822; 435/853-857; 435/885
[58] Field of Search .................... 424/93.3, 93.4, 424/93.44, 93.45; 426/43, 62, 71, 658; 435/252.4, 822, 853-857, 885

[56] References Cited

U.S. PATENT DOCUMENTS

| | | | |
|---|---|---|---|
| 4,298,619 | 11/1981 | Mutai et al. ........................ | 426/43 |
| 4,588,595 | 5/1986 | Okonogi et al. ..................... | 435/252.4 |
| 4,859,488 | 8/1989 | Kan et al. .......................... | 426/658 |
| 4,913,913 | 4/1990 | Takano et al. ...................... | 426/43 |
| 5,143,845 | 9/1992 | Masuda . | |
| 5,230,912 | 7/1993 | Yajima et al. ...................... | 426/43 |
| 5,531,989 | 7/1996 | Paul .................................. | 424/93.4 |
| 5,676,985 | 10/1997 | Fletcher et al. ..................... | 426/36 |
| 5,716,615 | 2/1998 | Cavalier Vesely et al. .......... | 424/93.4 |

FOREIGN PATENT DOCUMENTS

| | | |
|---|---|---|
| 0 529 414 | 3/1993 | European Pat. Off. . |
| 0 555 618 | 8/1993 | European Pat. Off. . |
| 0 577 904 | 1/1994 | European Pat. Off. . |
| 622024 | 11/1994 | European Pat. Off. . |
| 0 667 106 | 8/1995 | European Pat. Off. . |
| 4103755 | 5/1992 | Germany . |

OTHER PUBLICATIONS

Derwent Abstract, AN 91-105635, JP 03 047 035, Feb. 28, 1991.

Hawley, G.G. The Condensed Chemical Dictionary, 10th ed., p. 759, 1981.

*Primary Examiner*—Leon B. Lankford, Jr.
*Assistant Examiner*—Christopher R. Tate
*Attorney, Agent, or Firm*—Oblon, Spivak, McClelland, Maier & Neustadt, P.C.

[57] ABSTRACT

The invention relates to a composition for feed use containing a mixture of lyophilized live bacteria comprising at least two species of bacteria selected from *Bifidobacterium breve, Bifidobacterium infantis, Bifidobacterium longum* and *Bifidobacterium bifidum* and at least two species of bacteria selected from *Lactobacillus acidophilus, Streptococcus thermophilus, Lactobacillus bulgaricus, Lactobacillus casei, Lactobacillus plantarum* and *Streptococcus faecium* and one or more oligosaccharides.

16 Claims, No Drawings

COMPOSITION FOR FEED USE COMPRISING LYOPHILIZED LIVE LACTIC BACTERIA

FIELD AND BACKGROUND OF THE INVENTION

The present invention relates to a composition for feed use comprising lyophilized live probiotic bacteria, to the use of said composition as a supplement to foodstuffs, as well as to a kit comprising two containers respectively holding a foodstuff and said composition intended for being added to said foodstuff at the moment of being consumed.

It is known that some bacteria species are considered as "probiotic", in that they perform beneficial functions for the human organism when they are present in a live and viable form in the intestinal bacterial flora.

For example some probiotic bacteria, such as the lactic bacteria specific to yoghurt (that is *Lactobacillus bulgaricus* and *Streptococcus thermophilus*) stimulate the immune system, produce antagonist effects against pathogenic microorganisms, improve lactose digestion, perform a lipolytic activity making fats more digestible, reduce plasmatic values of cholesterol, protect the intestinal mucosa ensuring an even assimilation of the nutritive substances, produce polysaccharides that are active on some tumors and reduce viability of some enzyme-producing microorganisms catalysing conversion of procarcinogen substances into carcinogen substances.

Other probiotic bacteria producing some of the above mentioned beneficial effects and/or contributing in a synergic manner to production of these effects and in addition producing other beneficial effects are Bifidobacteria, *Lactobacillus acidophilus*, *Lactobacillus casei*, *Lactobacillus plantarum* and *Streptococcus faecium*.

For instance, Bifidobacteria, in addition to stimulating the immune system, reduce the amounts of ammonia and cholesterol in the blood, promote absorption of minerals and exert a competitive exclusion of pathogenic and putrefactive bacteria. In addition, Bifidobacteria are deemed to exert a preventive action against the colon cancer, in that these bacteria (and more particularly *Bifidobacterium bifidum*) reduce the activity of those enzymes that convert procarcinogen substances into carcinogen substances. The last-mentioned action is performed also by *Lactobacillus acidophilus* and *Lactobacillus casei*.

Synthesis of B-group vitamins, folic acid and antioxidants, due to the action of some of the above mentioned probiotic bacteria, represents a further beneficial effect.

Only some of the above mentioned probiotic bacteria have an endogenic origin in the intestinal flora. Moreover, the intestinal bacterial flora can be reduced, become unbalanced or be eliminated not only in individuals that have been submitted to antibiotic treatments or other therapies, or suffering from inflammatory intestinal diseases, but also in apparently healthy individuals. In addition, it is for example known that concentration of Bifidobacteria in the intestines is reduced with age, which will give rise to an increase in the concentration of pathogenic and putrefactive bacteria.

It is therefore important that not only probiotic bacteria that do not have an endogenic origin should be introduced into the intestinal flora, but also that the presence of the different probiotic bacteria, in a live and viable form, should be ensured in the intestinal flora, which probiotic bacteria should have appropriate concentrations and respect suitable proportions between the different species so that they may exert synergic and balanced actions between each other, to advantage of the host's health.

Some pharmaceutical compositions containing probiotic bacteria have been proposed either to reduce imbalances in the intestinal flora or to prevent or treat some diseases. However, these pharmaceutical compositions, exactly due to the fact that they are pharmaceutical compositions, are only used occasionally and for short periods of time, and therefore do not solve the problem of increasing, supplementing and balancing the intestinal flora in a permanent and prolonged manner.

In the light of the above and taking into account the fact that in recent years there is on the part of consumers an increasing demand of foodstuffs that, in addition to having a nutritional value, also have a positive impact on health, the Applicant has identified a new problem.

More particularly, the Applicant has identified the problem of making the use of foodstuffs containing live probiotic bacteria more easily accessible to and frequent and usual with any consumers, either in good health or ill, for the purpose of increasing, supplementing and balancing the intestinal flora, which will bring about advantages in terms of everyday health and prevention of diseases.

In particular, the Applicant has identified the problem of putting on the feed market compositions containing mixtures of different live probiotic bacteria, which are capable of reaching the intestines in a live and viable form, settling in the bacterial flora and growing, thereby performing important beneficial actions for the human health.

Another problem taken into consideration by the Applicant is to formulate a composition comprising a mixture of probiotic bacteria that are selected, as regards species and proportions thereof, in such a manner as to perform their beneficial functions in a synergic manner.

SUMMARY OF THE INVENTION

The above and other problems are solved by the present invention, the object of which is a composition for feed use comprising the following components:

(A) a mixture of lyophilized live bacteria comprising at least two species of bacteria selected from *Bifidobacterium breve, Bifidobacterium infantis, Bifidobacterium longum* and *Bifidobacterium bifidum* and at least two species of bacteria selected from *Lactobacillus acidophilus, Streptococcus thermophilus, Lactobacillus bulgaricus* and *Lactobacillus casei;*

(B) one or more oligosaccharides;

said component (A) being present in an amount of 4 to 20 parts by weight and said component (B) being present in an amount of 5 to 22 parts by weight.

DESCRIPTION OF THE PREFERRED EMBODIMENTS

For preparation of the bacteria mixture forming component (A), known strains of the above defined species can be used. Particularly advantageous results are achieved by using the following strains:

*Bifidobacterium breve*: LMG P-17501
*Bifidobacterium infantis*: LMG P-17502
*Bifidobacterium longum*: LMG P-17500
*Bifidobacterium bifidum*: LMG P-17499
*Lactobacillus acidophilus*: LMG P-17503
*Streptococcus thermophilus*: LMG P-17225

*Lactobacillus bulgaricus*: LMG P-17224

*Lactobacillus casei*: LMG P-17504

*Lactobacillus plantarum*: ATCC 8014

*Streptococcus faecium*: I-1671

Said strains indicated by "LMG P-" are deposited with the BCCM/LMG collection of the University of Gent, Ledeganokstraat 36, B-9000 Gent, Belgium.

Strain ATCC 8014 is deposited with American Type Culture Collection U.S.A.

Strain I-1671 is deposited with CNCM—Collection Nationale de Cultures de Microorganismes—Institut Pasteur.

Particularly advantageous results are achieved if cultures of high concentrations expressed in CFU/g (CFU meaning colony forming units) are used, and more particularly the following concentrations are preferred:

*Bifidobacterium breve*: at least $50 \times 10^9$ CFU/g, more preferably 100 to $150 \times 10^9$ CFU/g

*Bifidobacterium infantis*: at least $50 \times 10^9$ CFU/g, more preferably 10 to $150 \times 10^9$ CFU/g

*Bifidobacterium longum*: at least $50 \times 10^9$ CFU/g, more preferably 100 to $150 \times 10^9$ CFU/g

*Bifidobacterium bifidum*: at least $50 \times 10^9$ CFU/g, more preferably 100 to $150 \times 10^9$ CFU/g

*Lactobacillus acidophilus*: at least $100 \times 10^9$ CFU/g, more preferably 150 to $250 \times 10^9$ CFU/g

*Streptococcus thermophilus*: at least $50 \times 10^9$ CFU/g, more preferably 100 to $150 \times 10^9$ CFU/g

*Lactobacillus bulgaricus*: at least $5 \times 10^9$ CFU/g, more preferably 10 to $50 \times 10^9$ CFU/g

*Lactobacillus casei*: at least $10 \times 10^9$ CFU/g, more preferably 30 to $50 \times 10^9$ CFU/g.

*Lactobacillus plantarum*: at least $100 \times 10^9$ CFU/g, more preferably 150 to $250 \times 10^9$ CFU/g

*Streptococcus faecium*: at least $50 \times 10^9$ CFU/g, more preferably 100 to $150 \times 10^9$ CFU/g.

Cultures of the above stated concentrations are commercially available from Centro Sperimentale del Latte S.p.A.—Strada per Merlino, 3 —ZELO BUON PERSICO (Lodi)—Italy.

Preferably in the composition of the present invention, the overall concentration of bacteria forming component (A) is at least $50 \times 10^9$ CFU/g of component (A); more preferably it is at least $100 \times 10^9$ CFU/g of component (A).

The ratio by weight of one Bifidobacterium species to another Bifidobacterium species is preferably 0.75:1 to 1:1.25, more preferably about 1:1. Should *Streptococcus thermophilus* and *Lactobacillus bulgaricus* be both present, the ratio by weight of the former to the latter is preferably 1:1 to 10:1, more preferably 5:1 to 8:1. Practically the use of mixtures of *Streptococcus thermophilus* and *Lactobacillus bulgaricus* as commonly used for yoghurt production can be conceived.

In some preferred embodiments, component (A) in the composition of the present invention comprises:

either at least three species of bacteria selected from *Bifidobacterium breve, Bifidobacterium infantis, Bifidobacterium longum* and *Bifidobacterium bifidum*, or at least three species of bacteria selected from *Lactobacillus acidophilus, Streptococcus thermophilus, Lactobacillus bulgaricus, Lactobacillus casei, Lactobacillus plantarum* and *Streptococcus faecium*, or at least three species of bacteria selected from *Bifidobacterium breve, Bifidobacterium infantis, Bifidobacterium longum* and *Bifidobacterium bifidum* and at least three species of bacteria selected from *Lactobacillus acidophilus, Streptococcus thermophilus, Lactobacillus bulgaricus, Lactobacillus casei, Lactobacillus plantarum* and *Streptococcus faecium*.

In some cases it is preferred for *Bifidobacterium infantis* to be present in the composition of the present invention because in this way the composition has a very wide action spectrum which is beneficial both to adults and children.

A preferred composition is a composition in which component (A) consists of:

5 to 23% by weight, more preferably 7 to 14% by weight, of two or more bacteria selected from *Bifidobacterium breve, Bifidobacterium infantis, Bifidobacterium longum* and *Bifidobacterium bifidum*;

5 to 24% by weight, more preferably 8 to 14% by weight, of *Lactobacillus acidophilus*;

32 to 70% by weight, more preferably 40 to 62% by weight, of *Streptococcus thermophilus* and/or *Lactobacillus bulgaricus*;

0 to 40% by weight, more preferably 13 to 37% by weight of at least one bacterium selected from *Lactobacillus casei, Lactobacillus plantarum* and *Streptococcus faecium*.

Another preferred composition is a composition wherein component (A) consists of:

7 to 23% by weight, more preferably 10 to 21% by weight, of two or more bacteria selected from *Bifidobacterium breve, Bifidobacterium infantis, Bifidobacterium longum* and *Bifidobacterium bifidum*;

8 to 24% by weight, more preferably 10 to 21% by weight, of *Lactobacillus acidophilus*;

35 to 70% by weight, more preferably 45 to 65% by weight, of a mixture of *Streptococcus thermophilus* and *Lactobacillus bulgaricus*.

The composition of the present invention combines several different species of probiotic bacteria together and utilizes all properties of same in a synergic manner. For example, it has been found that the presence of lactic acid bacteria of yoghurt (*Streptococcus thermophilus* and *Lactobacillus bulgaricus*) is particularly useful for the purpose of improving viability and enhancing growing of other bacteria species, such as Bifidobacteria, *Lactobacillus acidophilus* and *Lactobacillus casei*. In addition, lactic acid bacteria of yoghurt can hydrolyze oligosaccharides that are already present in the organism and that are introduced together with component (B) of the composition of the present invention, releasing sugars that are useful for enhancing growth of Bifidobacteria and other beneficial bacteria.

Component (B) of the composition of the present invention consists of one or more oligosaccharides.

Suitable oligosaccharides are, for example: oligofructoses, galacto-oligosaccharides, lactosucrose, palatinose-oligosaccharides, glycosyl sucrose, malto-oligosaccharides, iso-malto-oligosaccharides, cyclodextrins, gentio-oligosaccharides, soybean-oligosaccharides and xylo-oligosaccharides. Particularly advantageous results are achieved with oligofructoses.

Particularly appropriate oligosaccharides are inulin and inulin-oligofructose. Examples of said products are the inulin and the inulin-oligofructose produced by the Belgian Company ORAFTI S.A. and put on the market under the names Raftline™ and Raftilose™, respectively.

Component (B) in the composition of the present invention solves the problem of keeping the different bacteria of component (A) in a good viability state along the digestive tract until the colon, as well as facilitating selection and settling of these bacteria in the intestines (that is an environment wherein a local microflora already exists).

Oligosaccharides are not degraded (or they are only partly degraded), are not absorbed or metabolized along the digestive tract until the colon and they have been found to constitute a vehicle and a substrate particularly appropriate for viability preservation and development of probiotic bacteria of component (A). Therefore, oligosaccharides of component (B) can be called "prebiotic" compounds.

In accordance with the present invention, association of the probiotic bacteria of component (A) with the oligosaccharides of component (B) enables a modification in the composition of the intestinal flora, by shifting the different species proportions in favor of the most probiotic species. For instance, there are many oligosaccharides that are preferentially used by Bifidobacteria as carbon and energy sources and therefore they promote a selective development of Bifidobacteria.

Said positive influence on Bifidobacteria development is particularly performed by inulin. In addition, Bifidobacteria metabolize inulin thereby producing volatile fat acids that help in meeting humans' energy requirements. These volatile fat acids also affect lipid metabolism (causing reduction in the cholesterol values) and glucose metabolism (causing glucose tolerance to increase).

The composition of the present invention preferably contains 5 to 12 parts by weight of component (A) and 8 to 15 parts by weight of component (B).

The composition of the present invention may also contain a component (C) consisting of sugar or an artificial sweetener. The optional sugar amount in the composition preferably is of 2 to 35 parts by weight, more preferably of 5 to 30 parts by weight. The artificial sweetener may be aspartame, saccharin, acesulfame, or combinations of aspartame+acesulfame.

In addition, the composition of the present invention may also contain a component (D) consisting of a disperser in the form of powder, particles or fibers of natural products. The optional amount of component (D) is preferably of 40 to 80 parts by weight, more preferably of 45 to 75 parts by weight.

Component (D) may be useful for enhancing the organoleptic features of the composition and/or increasing its nutritional power, in that it may consist of natural products containing vitamins and mineral salts. For example, component (D) may consist of powder, particles or fibers of products selected from cereals, malt extract (optionally in combination with cacao and egg), ginseng, chocolate, vanilla and vegetable extracts, hazelnuts and/or walnuts and/or almonds and/or macaroons to a granular state.

In selecting the possible artificial sweetener (C) and disperser (D), care should be taken in excluding products that are toxic or have an inhibitory effect on bacteria present in component (A).

The composition of the present invention has been conceived for being added to liquid, creamy or pasty foodstuffs, for the purpose of obtaining foods of high probiotic value.

Foodstuffs to which the composition of the present invention can be added are products of milk and dairy industry (milk, milk-based products, milk derivatives) and products based on (or derived from) vegetable products (in particular fruit).

In particular the Applicant has found that it is preferable for the composition of the present invention to be added to said foodstuffs directly by the consumer at the moment of use, and not by the producer during the manufacturing cycle of the foodstuffs or when they are packaged.

Another object of the present invention is therefore the use of the composition of the present invention as a supplement to a liquid, creamy or pasty foodstuff, said foodstuff being a milk, a milk-based or milk-derived product, a product based on or derived from vegetable products, said supplementation being carried out at the moment the foodstuff is being consumed.

The composition is added to the foodstuff preferably in such a manner that a proportion of 0.1–3.0 g of component (A) per 100 g of foodstuff, more preferably of 0.2–1.0 g of component (A) per 100 g of foodstuff, most preferably of 0.4–0.7 g of component (A) per 100 g of foodstuff, is reached. By these supplements, in the final foodstuff, overall concentrations of probiotic bacteria up to $600 \times 10^9$ CFU per 100 g of foodstuff can be achieved.

For example, the composition of the present invention can be added to a milk type, a yoghurt (of the natural type or supplemented with fruit), or another type of fermented milk, a milk-based dessert (for instance chocolate, coffee or vanilla), a milk-based beverage or a beverage based on milk serum or permeate enriched with fruit, a fruit juice (fruit being, for example, apricot, peach, pear, apple, bilberry, tropical fruits), a tomato juice, a carrot juice, tea (natural tea or peach tea) or a beverage based on vegetable extracts.

The composition of the present invention is useful because it can be added both to foodstuffs that do not contain probiotic bacteria (for the purpose of giving these products a probiotic value as well) and to foodstuffs already containing some probiotic bacteria (for the purpose of enhancing and/or completing their probiotic value).

Particularly advantageous is addition to foodstuffs such as milk, milk-based or milk-derived products. Actually, some bacteria of component (A) are lactic bacteria and therefore they find their natural environment in these types of foodstuffs. In addition, in some products such as yoghurt and fermented milks, bacteria of component (A) are introduced into environments already containing bacteria of the same species.

As already said above, it is preferable for the composition of the present invention to be supplemented at the moment that the foodstuff is being consumed. Actually, if the composition should be added during the production cycle of the foodstuff or when the foodstuff is being packaged, many bacteria of the composition should not keep a live and viable form during the foodstuff preservation. This decay would take place to a different extent depending on the particular bacterium species, the particular food type and the preservation conditions adopted therefor. On the other hand, bacteria of some species could also grow and prevail over the others. As a result, the overall amount of probiotic bacteria and the proportions of same at the moment of use of the foodstuff would be different from those of the composition with which the foodstuff had been initially supplemented. In other words, it would be impossible to ensure that at the moment of use the foodstuff will contain all probiotic bacteria in the desired amounts and proportions.

In addition, if the composition of the present invention would be added to foodstuffs before the latter are commercialized, some bacteria could cause fermentations, resulting in formation of or increase in acidity. In this way some foodstuffs would be unacceptable from an organoleptic point of view. This would happen not only in desserts and fruit juices (which have a neutral pH), but also in yoghurts that would take a too sour taste. By supplementing the foodstuff with the composition at the moment of consuming it, the consumer does not feel any sour taste because the ingested bacteria acquire viability again once settled in the Intestines, where they grow in a selective manner.

It should be also noted that Bifidobacteria, that are essential components in the composition of the present invention, survive with difficulty in an acid environment. Therefore, the amount of them would be greatly reduced during the foodstuff preservation period, due to the acidity caused by said fermentations, above all in the case of products that are slightly acid by themselves such as yoghurts.

The composition of the present invention can be preserved, by packaging it under highly hygienic conditions, within any container protecting it from contact with air and humidity and, if possible, from direct light, at the temperature of a common home refrigerator (that is a temperature of 2-8°C.) over a time as long as one year. During preservation, until the moment of use, the amounts and proportions of live bacteria present in the composition stay unchanged.

The composition of the present invention can be commercialized separately from the foodstuff with which it can be mixed. However, the Applicant has conceived a new kind of commercial article solving the problem of facilitating, enhancing and spreading consumption of foodstuffs useful for the organism welfare and prevention and treatment of some diseases. This new kind of commercial article is a further object of the present invention and it consists of a kit comprising:

- a container X holding a liquid, creamy or pasty foodstuff, said foodstuff being milk, a milk-based product, a milk derivative, a product based on vegetable products or derived from vegetable products, and
- a container Y holding a composition in accordance with the invention, both said containers being closed and openable at the moment of consuming said foodstuff, and said container Y being arranged for the purpose of supplementing said foodstuff with the composition contained therein, at the moment of consuming it.

The composition of the present invention which is held in container Y preferably contains 0.1-3.0 g, more preferably 0.2-1.0 g, most preferably 0.4-0.7 g of component (A) (that is a mixture of lyophilized live bacteria) per 100 g of foodstuff held in container X.

Particular examples of foodstuffs that can be held in container X are the same as listed above with reference to the use of the composition of the present invention.

The above kit must be preserved to the temperature at which the composition held in container Y is to be maintained, over periods of time of 30-40 days in the case of milk-based fresh products, or 4-6 months in the case of long-life foodstuffs. Once said kit has been purchased, it can be preserved in a common home refrigerator and can be used at any moment until the due date of the foodstuff held in container X, by opening both containers and mixing contents of same at the moment that one wishes to consume the foodstuff.

Should the kit be, by chance, maintained until a date after the due date of the foodstuff, the probiotic live bacteria mixture held in container Y can be used by mixing it at the moment of use with any liquid, creamy or pasty foodstuff (by mixing it even with water, for example)

It is apparent from the above that the use of the composition and kit of the present invention is simple, flexible and very useful, because it promotes the human organism welfare, by normalizing and enhancing the intestinal flora functions. Among other things, the use of this composition promotes synthesis of vitamins and proteins, facilitates digestive processes, prevents colonization and growing of pathogenic bacteria, stimulates the immune response and contributes to reduction of the cholesterol amount.

The following examples are given for illustrating some embodiments of the invention, without however limiting the extent of same.

EXAMPLES

Bacteria strains and concentrations of the respective lyophilized cultures of live bacteria used in the following examples are:

*Bifidobacterium breve*: LMG P-17501; concentration $130 \times 10^9$ CFU/g

*Bifidobacterium infantis*: LMG P-17502; concentration $130 \times 10^9$ CFU/g

*Bifidobacterium longum*: LMG P-17500; concentration $130 \times 10^9$ CFU/g

*Bifidobacterium bifidum*: LMG P-17499; concentration $400 \times 10^9$ CFU/g

*Lactobacillus acidophilus*: LMG P-17503; concentration $200 \times 10^9$ CFU/g

*Streptococcus thermophilus*: LMG P-17225; concentration $130 \times 10^9$ CFU/g

*Lactobacillus bulgaricus*: LMG P-17224; concentration $30 \times 10^9$ CFU/g

*Lactobacillus casei*: LMG P-17504; concentration $40 \times 10^9$ CFU/g

*Lactobacillus plantarum*: ATCC 8014; concentration $200 \times 10^9$ CFU/g

*Streptococcus faecium*: I-1671; concentration $130 \times 10^9$ CFU/g

EXAMPLE 1

A mixture (component A of the composition of the present invention) is prepared, which consists of:

20% by weight of a mixture of *Bifidobacterium breve*, *Bifidobacterium infantis* and *Bifidobacterium longum* (in a ratio of 1:1:1)

20% by weight of *Lactobacillus acidophilus*

60% by weight of a yoghurt culture consisting of a mixture of *Streptococcus thermophilus* and *Lactobacillus bulgaricus* (in a ratio of 5:1).

The overall concentration of bacteria present in said component (A) is about $134 \times 10^9$ CFU/g.

Then a composition is prepared which contains 40% by weight of said component A and 60% by weight of inulin (component B), produced by the Belgian Company ORAFTI S.A. and commercialized under the name Raftline™.

In said composition the overall bacteria concentration, due to component (A) is about $54 \times 10^9$ CFU/g of composition.

Afterwards, 30 doses of said composition are prepared, each weighing 1.5 g, and they are closed in sealed containers and preserved in a common home refrigerator. Also preserved in the same refrigerator are 10 packages of 125 g of milk-based or milk-derived products (namely, 3 natural yoghurts, 4 fruit-supplemented yoghurts, 1 chocolate dessert, 1 coffee dessert and 1 vanilla dessert), and 10 packages of different beverages (namely, grapefruit, orange, apricot, peach, pear, apple, bilberry and tropical fruit juices, one tea and one peach tea).

After 20 days, the 10 packages of milk-based or milk-derivative products and 10 doses of said composition in accordance with the present invention are taken out of the refrigerator and, immediately before consuming them, each product of the 10 packages is supplemented with each dose of the composition.

After short stirring, the different products are tasted; taste of same is very palatable and fresh, and neither taste contrasts nor anomalous aftertastes are noticed. The overall structure of the product after mixing is immediately adapted for use.

The overall concentration of the different bacteria present after mixing in each package of 125 g of product without taking into account bacteria possibly already present in the product itself) is about $64 \times 10^9$ CFU per 100 g of product.

After a further period of 20 days, the 10 packages of different beverages and 10 doses of said composition in accordance with the present invention are taken out of the refrigerator. The 10 packages of beverages are opened and each of them is used for filling a glass with 150 g of beverage. Immediately before use, each dose of the composition is added to each beverage held in the 10 glasses. The overall concentration of the different bacteria present in the beverages after said supplement is about $53.6 \times 10^9$ CFU per 100 g of beverage.

After short stirring, the various beverages are tasted; their taste is very palatable and fresh and neither taste contrasts nor anomalous aftertastes are noticed. The overall structure of the product after mixing is immediately adapted for use.

After a further period of 60 days, the remaining 10 doses of said composition are taken out of the refrigerator and content of same is analyzed through determination of overall bacterial count for each individual species used, by means of specific culture media: in all doses concentration of bacteria and viability of same has remained unchanged.

EXAMPLE 2

Preparation of a mixture (component A of the composition of the present invention) is carried out which consists of:

8.2% by weight of a mixture of *Bifidobacterium breve, Bifidobacterium infantis* and *Bifidobacterium longum* (in a ratio of 1:1:1)

10.2% by weight of *Lactobacillus acidophilus*

55.9% by weight of a yoghurt culture, consisting of a mixture of *Streptococcus thermophilus* and *Lactobacillus bulgaricus* (in a ratio of 8:1)

25.7% by weight of *Lactobacillus casei*.

The overall concentration of bacteria present in said component (A) is about $108 \times 10^9$ CFU/g.

Then a composition is prepared which contains:

6% by weight of said component A

10% by weight of the same inulin as used in Example 1 (component B)

10% by weight of sugar (component C)

74% by weight of cereals in the form of powder (component D).

In said composition the overall bacteria concentration, due to component (A) is about $6.5 \times 10^9$ CFU/g of composition.

Then 30 doses of said composition are prepared, each weighing 10 g and they are closed in sealed containers and maintained in a common home refrigerator, together with 10 packages of milk-based or milk-derivative products (of the same type as in Example 1) and 10 packages of beverages (of the same type as in Example 1).

All modalities of the following experimentation are the same as in Example 1.

The overall concentration of the various bacteria present after mixing in each package of milk-based or milk-derivative product (without taking into account bacteria already present in the product itself) and in each glass of beverage are about $52 \times 10^9$ CFU per 100 g of product and about $43.3 \times 10^9$ CFU per 100 g of beverage, respectively.

In this case too, the properties of the various products and beverages, once supplemented with the 10 g doses of the composition of the present invention appear to be excellent. The same is true as regards properties of the other 10 composition doses not used and left in the refrigerator.

EXAMPLE 3

Example 2 is repeated using the same bacteria mixture (component A) and following the same experimental modalities.

The only difference is that in this case the composition of the present invention contains:

6% by weight of component A of Example 2

10% by weight of the same inulin as used in Example 1 (component B)

34% by weight of sugar (component C)

50% by weight of malt extract (component D).

In this case too the properties of the various products and beverages, once supplemented with the 10 g doses of the composition of the present invention appear to be excellent. The same is true as regards the properties of the further 10 composition doses not used and left in the refrigerator.

EXAMPLE 4

Example 3 is repeated following the same experimental modalities.

The only difference is that in this case the mixture of bacteria (component A) consists of:

8.5% by weight of a mixture of *Bifidobacterium breve, Bifidobacterium infantis, Bifidobacterium longum* and *Bifidobacterium bifidum* (in a ratio 1:1:1:1)

10.2% by weight of *Lactobacillus acidophilus*

46.0% by weight of a yoghurt culture consisting of a mixture of *Streptococcus thermophilus* and *Lactobacillus bulgaricus (in a ratio* 7:1)

20.4% by weight of *Lactobacillus casei*

14.9% by weight of a mixture of *Lactobacillus plantarum* and *Streptococcus faecium* (in a ratio 1:1).

In this case too the properties of the various products and beverages, once supplemented with the 10 g doses of the composition of the present invention appear to be excellent. The same is true as regards the properties of the further 10 composition doses not used and left in the refrigerator.

EXAMPLES 5 TO 8

Examples 1, 2, 3 and 4 are repeated following the same experimentation modalities, with the only difference that component B of the composition consists of oligofructose produced by the Belgian Company ORAFTI S.A. and commercialized under the name Raftilose™.

In these Examples too the properties of the various products and beverages, once supplemented with the compositions of the present invention, appeared excellent. The same is true for the properties of the composition doses not used and left in the refrigerator.

EXAMPLES 9 TO 16

Examples 1 to 8 are repeated following the same experimentation modalities, with the only difference that three milk packages of different types are maintained in the refrigerator, to which after ten days the compositions of the present invention are added, at the moment of use. The properties of the various milk types, once supplemented with the compositions of the present invention, appear excellent.

What is claimed is:

1. A composition for feed use, consisting essentially of:
   (A) a mixture of lyophilized live bacteria comprising at least two species of bacteria selected from the group consisting of *Bifidobacterium breve, Bifidobacterium infantis, Bifidobacterium longum* and *Bifidobacterium bifidum*, and at least two species of bacteria selected from the group consisting of *Lactobacillus acidophilus, Streptococcus thermophilus, Lactobacillus bulgaricus, Lactobacillus bulgaricus, Lactobacillus casei, Lactobacillus plantarum* and *Streptococcus faecium*;
   (B) one or more oligosaccharides selected from the group consisting of inulin and fructooligosaccharides;
   (C) a disperser in the form of a powder, particles or fibers of edible, ingestible natural products selected from the group consisting of cereals, malt extract, ginseng, chocolate, vanilla and vegetable extracts; and
   (D) optionally, sugar or an artificial sweetener;
   wherein the composition contains 5 to 12 parts by weight of (A) and 8 to 15 parts by weight of (B);
   wherein the concentration of the bacteria in (A), when present, are as follows:
   *Bifidobacterium breve:* 100 to $150 \times 10^9$ CFU/g,
   *Bifidobacterium infantis:* 100 to $150 \times 10^9$ CFU/g,
   *Bifidobacterium longum:* 100 to $150 \times 10^9$ CFU/g,
   *Bifidobacterium bifidum:* 100 to $150 \times 10^9$ CFU/g,
   *Lactobacillus acidophilus:* 100 to $250 \times 10^9$ CFU/g,
   *Streptococcus thermophilus:* 100 to $150 \times 10^9$ CFU/g,
   *Lactobacillus bulgaricus:* 10 to $50 \times 10^9$ CFU/g,
   *Lactobacillus casei:* 30 to $50 \times 10^9$ CFU/g,
   *Lactobacillus plantarum:* 150 to $250 \times 10^9$ CFU/g,
   *Streptococcus faecium:* 100 to $150 \times 10^9$ CFU/g; and
   and wherein the overall concentration of bacteria in (A) is at least $100 \times 10^9$ CFU/g of (A).

2. The composition as claimed in claim 1, wherein (A) consists of:
   5 to 23% by weight of two or more bacteria selected from the group consisting of *Bifidobacterium breve, Bifidobacterium infantis, Bifidobacterium longum* and *Bifidobacterium bifidum*;
   5 to 24% by weight of *Lactobacillus acidophilus*;
   32 to 70% by weight of *Streptococcus thermophilus* and/or *Lactobacillus casei, Lactobacillus plantarum* and *Streptococcus faecium*, and
   0 to 40% of at least one bacterium selected from the group consisting of *Lactobacillus casei, Lactobacillus plantarum*, and *Streptococcus faecium*.

3. The composition as claimed in claim 1, wherein the weight ratio of one species of Bifidobacterium to another species of Bifidobacterium is 0.75:1 to 1:1.25.

4. The composition as claimed in claim 1, wherein when the composition contains *Streptococcus thermophilus* and *Lactobacillus bulgaricus*, the weight ratio of the former to the latter is 1:1 to 10:1.

5. The composition as claimed in claim 1 comprising 40 to 80 parts by weight of (C).

6. The composition as claimed in claim 1, comprising 2 to 35 parts by weight of said sugar.

7. A food composition, comprising a foodstuff and the composition as claimed in claim 1.

8. The food composition of claim 7, which contains which contains 0.2 to 1.0 g of (A) per 100 g of the foodstuff.

9. A method of supplementing a foodstuff, comprising adding and mixing the composition of claim 1 to a foodstuff just prior to eating said foodstuff.

10. The method of claim 9, wherein said foodstuff is a milk, a milk-based or milk-derived product, or a product based on or derived from vegetable products.

11. The method of claim 9, wherein said foodstuff is a milk, a yoghurt or another type of fermented milk, a milk-based dessert or a milk-based beverage or a beverage based on milk serum or milk permeate enriched with fruit, a fruit juice, a tomato juice, a carrot juice, a tea, or a beverage based on vegetable extracts.

12. The method of claim 9, wherein 0.2 to 1.0 g of (A) is added to 100 g of the foodstuff.

13. A kit, comprising:
   a first container which contains the composition of claim 1, and
   a second container which contains a foodstuff.

14. The kit of claim 13, wherein said foodstuff is a milk, a milk-based or milk-derived product, or a product based on or derived from vegetable products.

15. The kit of claim 13, wherein said foodstuff is a milk, a yoghurt or another type of fermented milk, a milk-based dessert or a milk-based beverage or a beverage based on milk serum or milk permeate enriched with fruit, a fruit juice, a tomato juice, a carrot juice, a tea, or a beverage based on vegetable extracts.

16. A composition for feed use, obtained by a process comprising combining:
   (A) a mixture of lyophilized live bacteria comprising at least two species of bacteria selected from the group consisting of *Bifidobacterium breve, Bifidobacterium infantis, Bifidobacterium longum* and *Bifidobacterium bifidum*, and at least two species of bacteria selected from the group consisting of *Lactobacillus acidophilus, Streptococcus thermophilus, Lactobacillus bulgaricus, Streptococcus thermophilus, Lactobacillus bulgaricus, Lactobacillus casei, Lactobacillus plantarum* and *Streptococcus faecium*;
   (B) one or more oligosaccharides selected from the group consisting of inulin and fructooligosaccharides;
   (C) a disperser in the form of a powder, particles or fibers of edible, ingestible natural products selected from the group consisting of cereals, malt extract, ginseng, chocolate, vanilla and vegetable extracts; and
   (D) optionally, sugar or an artificial sweetener;
   wherein the composition contains 5 to 12 parts by weight of (A) and 8 to 15 parts by weight of (B);
   wherein the concentration of the bacteria in (A), when present, are as follows:
   *Bifidobacterium breve:* 100 to $150 \times 10^9$ CFU/g,
   *Bifidobacterium infantis:* 100 to $150 \times 10^9$ CFU/g,
   *Bifidobacterium longum:* 100 to $150 \times 10^9$ CFU/g,
   *Bifidobacterium bifidum :* 100 to $150 \times 10^9$ CFU/g,
   *Lactobacillus acidophilus:* 100 to $250 \times 10^9$ CFU/g,
   *Streptococcus thermophilus:* 100 to $150 \times 10^9$ CFU/g,
   *Lactobacillus bulgaricus:* 10 to $50 \times 10^9$ CFU/g,
   *Lactobacillus casei:* 30 to $50 \times 10^9$ CFU/g,
   *Lactobacillus plantarum:* 150 to $250 \times 1^9$ CFU/g,
   *Streptococcus faecium:* 100 to $150 \times 10^9$ CFU/g; and
   wherein the overall concentration of bacteria in (A) is at least $100 \times 10^9$ CFU/g of (A); and
   wherein the composition consists essentially of (A), (B), (C), and, optionally, (D).

* * * * *